: US005630420A

United States Patent [19]

Vaitekunas

[11] Patent Number: 5,630,420
[45] Date of Patent: May 20, 1997

[54] ULTRASONIC INSTRUMENT FOR SURGICAL APPLICATIONS

[75] Inventor: Jeffrey J. Vaitekunas, West Chester, Ohio

[73] Assignee: Ethicon Endo-Surgery, Inc., Cincinnati, Ohio

[21] Appl. No.: 536,812

[22] Filed: Sep. 29, 1995

[51] Int. Cl.⁶ ......................................................... A61B 8/00
[52] U.S. Cl. ......................................................... 128/662.03
[58] Field of Search ........................ 128/660.03, 660.06, 128/662.03; 601/2; 606/1, 669

[56] References Cited

U.S. PATENT DOCUMENTS

| | | | |
|---|---|---|---|
| 5,112,300 | 5/1992 | Ureche | 604/22 |
| 5,180,363 | 1/1993 | Idemoto et al. | 202/32 |
| 5,269,309 | 12/1993 | Fort et al. | 128/661.01 |
| 5,438,554 | 8/1995 | Seyed-Bobrforosh et al. | 128/662.03 |
| 5,526,815 | 6/1996 | Granz et al. | 128/662.03 |

FOREIGN PATENT DOCUMENTS

| | | |
|---|---|---|
| 0624346A2 | 11/1994 | European Pat. Off. . |
| 2099049 | 4/1990 | Japan . |

*Primary Examiner*—George Manuel
*Attorney, Agent, or Firm*—Bernard E. Shay

[57] ABSTRACT

An improved surgical instrument is described wherein, an ultrasonic stack includes one or more piezoelectric sections surrounded by at least first resonator section and a second resonator section. The excitation signal for the ultrasonic stack is adapted to provide power at a first and a second frequency in order to drive the surgical tip of the instrument at a first frequency and second frequency simultaneously.

17 Claims, 7 Drawing Sheets

FIG. 7

ULTRASONIC INSTRUMENT FOR SURGICAL APPLICATIONS

FIELD OF THE INVENTION

The present invention relates, in general, to an improved ultrasonic surgical instrument and, more particularly, to an ultrasonic surgical instrument wherein the piezoelectric elements are driven at two or more excitation frequencies.

BACKGROUND OF THE INVENTION

Ultrasonic surgical instruments may be used in medical procedures to, for example, dissect or cut living organic tissue. The dissecting or cutting action is accomplished by a surgical implement at the distal end of the instrument, the surgical tip transmitting ultrasonic power to the tissue. Ultrasonic power may also be used to cauterize tissue surrounding the surgical tip, causing hemostasis by coagulating blood in the surrounding tissue.

Ultrasonic vibration is induced in the surgical tip by electrically exciting one or more piezoelectric elements in the instrument handpiece. The piezoelectric elements are excited at a resonant frequency of the surgical instrument. The fundamental resonant frequency of the surgical instruments described herein is $f_o$ and the resonant wavelength is $\lambda_o$. $\lambda_o$ is equal to $c/f_o$ where c is the speed of sound in the instrument. The electrical excitation signal being sinusoidal in nature or having a sinusoidal component, the piezoelectric elements generate a mechanical standing wave vibration at a frequency equal to the frequency of the electrical excitation signal. Vibrations generated by the piezoelectric section are filtered through a resonator, amplified by at least one velocity transformer and transmitted to the surgical tip.

In the ultrasonic surgical instruments described herein, the hand piece, which is also known as the "Langevin Stack" or "stack", includes at least one piezoelectric section surrounded by a pair of resonators. The resonators generally comprise metal sections which abut the piezoelectric section on each side and extend a distance of approximately one quarter wave length ($\lambda_o/4$) from the center of the piezoelectric stack. The stack, including the piezoelectric elements and the resonators, is approximately one-half wave length ($\lambda_o/2$) long. The resonators act as a mechanical bandpass filter, filtering out or substantially reducing acoustic waves at frequencies above or below the frequency of operation and above or below harmonics of the frequency of operation. One end of the stack may be adapted to receive the cable or wire which transmits the electrical excitation signal to the piezoelectric elements. In many such instruments, the resonators are electrically grounded and the excitation signal is connected to alternating pairs of piezoelectric elements within the stack. The opposite end of the stack is generally adapted to receive either the surgical tip or a transmission rod which is adapted to transmit the acoustic signal from the stack to a surgical tip.

In surgical instruments such as the instruments described above, the acoustic waves may be amplified by inserting "velocity transformers" between the resonator and the tip. A velocity transformer amplifies the acoustic wave by reducing the cross sectional area of the instrument. Therefore, by using a transmission rod with a smaller diameter than the resonator output, the junction between the resonator and the transmission rod acts as a velocity transformer, increasing the intensity of the acoustic wave transmitted through the transmission rod. Where the tip is smaller in diameter than the transmission rod, a similar step junction at the interface between the transmission rod and the tip acts as a second velocity transformer, further increasing the intensity of the acoustic wave at the tip of the instrument. Generally, the length of the resonators and transmission rods are chosen to ensure that the velocity transformers are located at nodes in the standing wave pattern.

As stated previously, an acoustic standing wave pattern is initiated by applying an electric voltage at a frequency f to the piezoelectric elements. The application of an electrical voltage across a piezoelectric element results in the expansion or contraction of the piezoelectric element along the axis of the voltage gradient. The direction of displacement of the piezoelectric element (i.e. whether it expands or contracts) is determined by the polarity of the signal applied. Thus, when an electrical excitation a signal with a sinusoidal component at a frequency f is applied, the piezoelectric elements expand and contract in a continuous manner. Mechanical expansion and contraction of the stack itself may be avoided by using the piezoelectric elements in pairs, where the application of an electric signal of a given polarity causes one element of the pair to expand and the second element of the pair to contract.

An ultrasonic surgical instrument may be driven or excited at any of its resonant frequencies. The instrument, having a fundamental resonant frequency of $f_o$ may be driven by an excitation signal $f_c$ at any harmonic (i.e. whole integer multiple) of $f_o$. A signal at the excitation frequency $f_c$ has a wavelength $\lambda_c$. Since the fundamental resonant frequency of the instrument is $f_o$, an electrical excitation signal wave which drives the piezoelectric elements at a frequency of $f_o$ will cause the surgical tip to vibrate at $f_o$. Where the electrical excitation signal is not a clean sine wave (e.g. a square or sawtooth wave) it includes harmonics of the excitation signal and the surgical tip would be expected to vibrate at $f_o$ and at harmonics of $f_o$. Even where the electrical excitation signal is a clean sine wave, nonlinearities in the instrument may cause the surgical tip to vibrate at $f_o$ and at harmonics of $f_o$. In either case, the magnitude of the vibration at the surgical tip would be greatest at $f_o$, and would be expected to be substantially smaller at harmonics of $f_o$. In most cases, the power at the harmonic frequency would be less than 25% of the power at the fundamental frequency. Thus, in known generators, power transmitted by the surgical tip at frequencies other than the excitation frequency would be expected to be at most 25% of the power transmitted at of the excitation frequency of the instrument. The relative power in the excitation frequency and its harmonics is a function of the degree to which the excitation signal deviates from a clean sine wave. Therefore, where the excitation signal drives the piezoelectric elements at $f_o$, substantially all the work done by the tip (e.g. cutting and/or cauterizing tissue) is being done at $f_o$. Where the excitation signal drives the piezoelectric elements at any other excitation frequency $f_e$, substantially all the work done by the tip is being done at $f_e$.

Certain vibration frequencies are believed to enhance the operation of an ultrasonic instrument for a particular purpose. For example, a given frequency may be particularly beneficial when using the instrument to cut or dissect tissue, while a second, different frequency, may be beneficial when using the instrument to cauterize tissue. Therefore, driving the piezoelectric elements at both a first excitation frequency, for example, the fundamental frequency of the instrument, and at one or more harmonics of the excitation frequency could, in some applications, substantially improve the performance of the instrument. For example, where the instrument is being used to cut and coagulate tissue, the excitation signal might be selectively controlled to provide power at the fundamental frequency for cutting tissue and at a harmonic of the fundamental frequency for cauterization the tissue.

Since the application of acoustic power to tissue in the form of ultrasonic waveforms tissue may result in different beneficial effects depending upon the frequency of the ultrasonic power applied to the tissue, it would be beneficial to design an ultrasonic surgical instrument where the piezoelectric stack is excited at both a first excitation frequency, for example, fundamental frequency of the instrument and at least one harmonic of the excitation frequency. It would further be beneficial to design an ultrasonic instrument wherein the power supplied at harmonics of the first excitation frequency is substantially equal to or greater than 50% of the power supplied at the first excitation frequency.

SUMMARY OF THE INVENTION

The present invention relates to an ultrasonic surgical instrument wherein the excitation signal drives the piezoelectric elements of the surgical instrument at a plurality of frequencies including a first frequency $f_1$ and a second frequency $f_2$ where $f_2$ is preferably a whole integer multiple of $f_1$. In one embodiment of the invention, the power of the excitation signal at the second frequency $f_2$ is substantially equal to or greater than the power of the excitation signal of the first frequency $f_1$. In a further embodiment of the present invention, the power of the excitation signal at the second frequency $f_2$ is equal to or greater than 50% of the power of the excitation signal at the first frequency $f_1$. In a further embodiment of the present invention, the power of the excitation signal at the first frequency $f_1$ is equal to or greater than 50% of the power of the excitation signal at the second frequency $f_2$. In a further embodiment at the present invention, frequency $f_2$ is twice frequency $f_1$. In a further embodiment of the present invention, the stack includes multiple piezoelectric sections, each section being driven at either a fundamental frequency or at a harmonic of the fundamental frequency such that the surgical tip vibrates at multiple frequencies.

BRIEF DESCRIPTION OF THE DRAWINGS

The novel features of the invention are set forth with particularity in the appended claims. The invention itself, however, both as to organization and methods of operation together with further objects and advantages thereof, may best be understood by reference to the following description, taken in conjunction with the accompanying drawings in which:

DETAILED DESCRIPTION OF THE PREFERRED EMBODIMENTS

Figure 1:
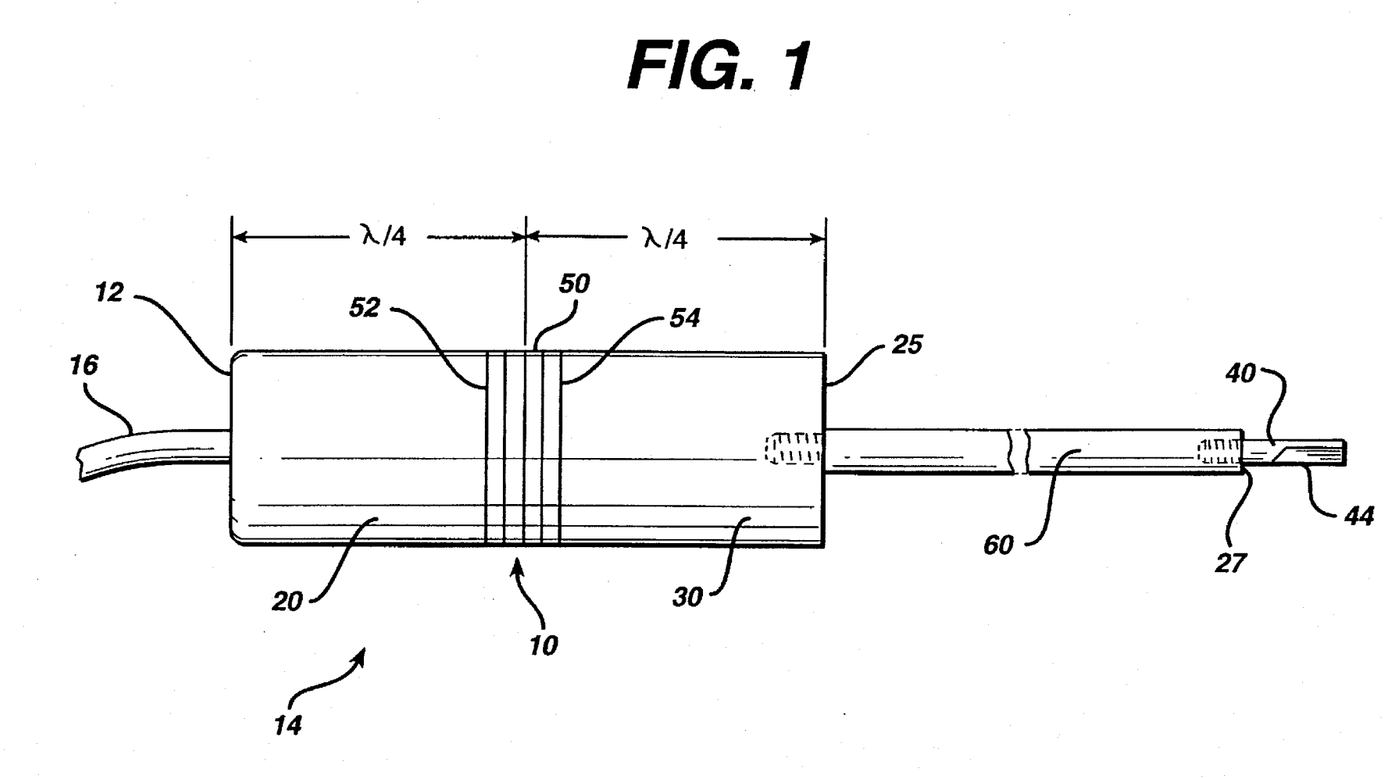
FIG. 1 is a side view of one embodiment of a surgical instrument including a single piezoelectric section.

FIG. 1 is a side view of a first embodiment of an ultrasonic surgical instrument according to the present invention. In the embodiment of the invention illustrated in FIG. 1, ultrasonic surgical instrument 14 includes stack 10 connected to surgical tip 40 through transmission rod 60. Signal wire 16 carries an electrical excitation signal to ultrasonic stack 10. Stack 10 is comprised of a first resonator 20 connected to a first side 52 of a piezoelectric section 50 and a second resonator 30 connected to a second side 54 of piezoelectric section 50. Transmission rod 60 couples the output of second resonator 30 to a surgical tip 40 which may include a blade 44 or other device for transmitting ultrasonic power to tissue. As illustrated in FIG. 1, transmission rod 60 is connected to second resonator 30 by securing transmission rod 60 into second resonator 30 using, for example, a threaded fitting. In FIG. 1, transmission rod 60 is smaller than resonator 30, forming step junction 25. Surgical tip 40 is connected to transmission rod 60 using, for example, a threaded fitting securing surgical tip 40 into transmission rod 60. Surgical tip 40 being smaller than transmission rod 60, step junction 27 is formed at the intersection between transmission rod 60 and surgical tip 40. Step junctions 25 and 27 act as velocity transformers, increasing the magnitude of the vibration passed to surgical tip 40.

Ultrasonic instrument 14 may include an outer casing (not shown) adapted to isolate the operator from vibrations in stack 10. Stack 10 supports and houses ultrasonic piezoelectric section or transducer assembly 50. In this embodiment piezoelectric section 50 includes one or more pairs of opposed piezoelectric crystals. The pairs of piezoelectric crystals are sandwiched together between a pair of spaced apart and opposing resonators 20 and 30. Piezoelectric section 50 vibrates, in response to high frequency electrical power supplied thereto from a control system such as the one illustrated in FIG. 6. When operated, piezoelectric section 50 produces high frequency mechanical vibrations which are transmitted to surgical tip 40 in a standing wave-pattern. Piezoelectric section 50 produces fundamental ultrasonic vibrations in a range of, for example, 10 kHz to 500 kHz, and, preferably, in a range of about 20 kHz to 80 kHz. Directly and centrally coupled to piezoelectric section 50 through second resonator 30 is an elongated vibration coupling or transmission rod 60. Transmission rod 60 is also coupled to surgical or operative tip 40. Transmission rod 60 may be formed with an aspiration conduit or passage (not shown) extending the axial extent thereof. The aspiration passage would fluidically interconnect at one end with a central bore (not shown) of operative tip 40 and at the other end to an aspiration conduit (not shown) leading from the handpiece to a suction pump (not shown). Operation of the suction pump would cause fragmented body tissue and fluids present at the surgical site to be aspirated through a central bore of surgical tip 40 and the handpiece assembly to a suitable collection vessel (not shown).

Figure 2:
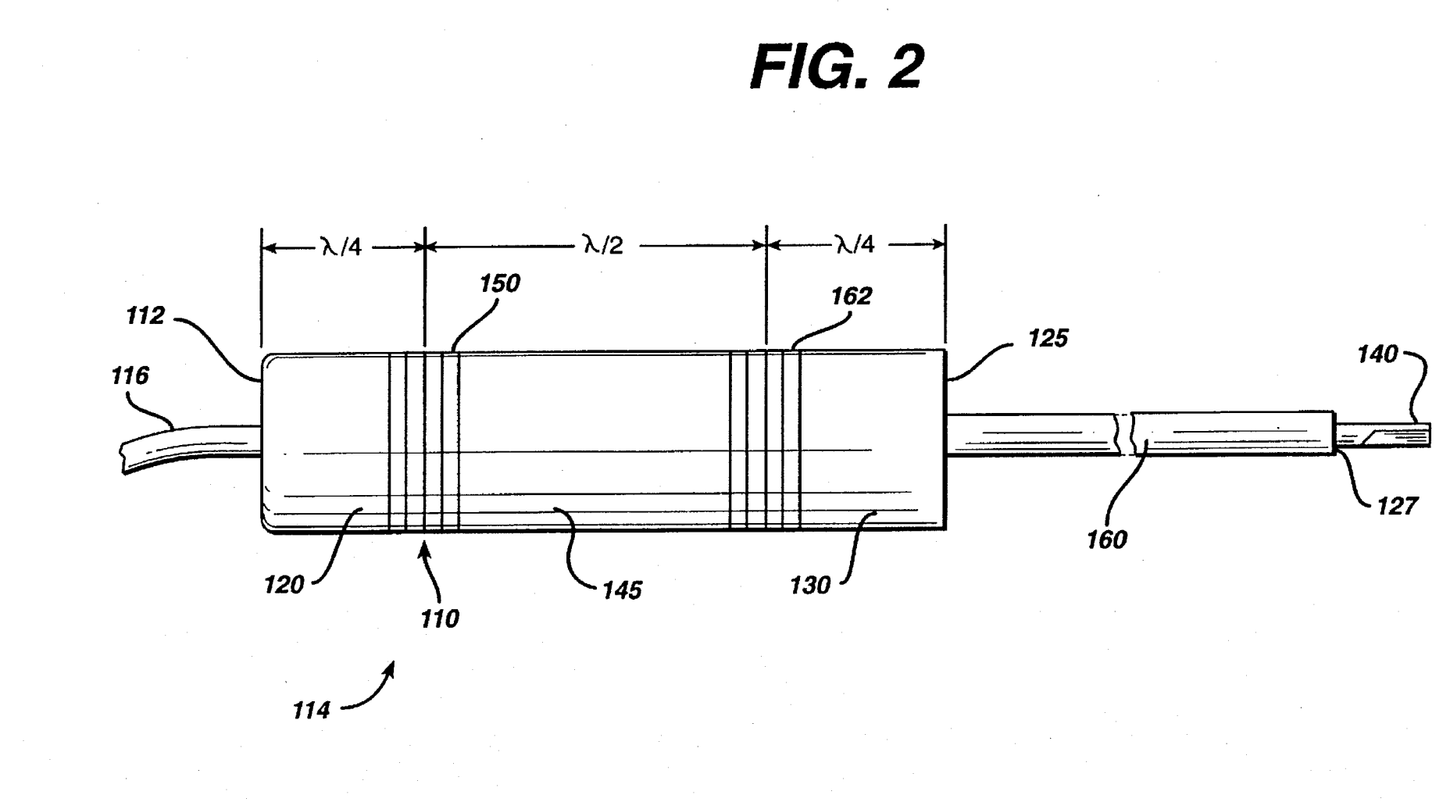
FIG. 2 is a side view of a further embodiment of a surgical instrument including two piezoelectric sections.

FIG. 2 is a side view of a second embodiment of an ultrasonic surgical instrument 114 according to the present invention. Ultrasonic surgical instrument 114 includes stack 110 connected to a surgical tip 140 through transmission rod 160. Ultrasonic surgical instrument 114 may include an outer casing adapted to isolate the operator from vibrations during use. In the embodiment of FIG. 2, stack 110 supports and houses first 150 and second 162 ultrasonic piezoelectric sections or transducer assemblies. In this embodiment, piezoelectric section 150 and 162 may include one or more pairs of opposed piezoelectric crystals. Piezoelectric sections 150 and 162 are separated by central section 145 and are sandwiched between spaced apart and opposing resonators 120 and 130. Central section 145 may comprise a substantially solid metallic region. Piezoelectric sections 150 and 160 are operable, in response to high frequency electrical power supplied through signal wire 116 from a control system, such as the one illustrated in FIG. 7 under the control of a footswitch or the like. When operated, piezoelectric sections 150 and 162 produce high frequency mechanical vibrations which are transmitted to surgical tip 140 in a standing wave-pattern. Piezoelectric sections 150 and 162 are operable to produce fundamental ultrasonic vibrations in a range of, for example, 10 kHz to 500 kHz, and, preferably, in a range of about 20 kHz to 80 kHz. Directly and centrally coupled to piezoelectric sections 150 and 162 through resonator 130 and central section 145 is an elongated vibration coupling or transmission rod 160. Transmission rod 160 is also coupled to surgical or operative tip 140. The embodiment illustrated in FIG. 2 may also include an aspiration passage, aspiration conduit and control bore in transmission rod 160, stack 110 and surgical tip 140 respectively.

In the embodiment of FIGS. 1 and 2, piezoelectric stacks 50, 150 and 160 comprise a plurality of piezoelectric elements. The electrical signal supplied by signal wire 16 and 116 excites the piezoelectric elements, causing them to vibrate and generate an ultrasonic acoustic wave as described herein. The signal supplied by signal wire 16 and 116 may be, for example, a signal having an rms voltage of approximately 500 volts with a current level of approximately ½ amp. The individual elements of stack 50, 150 and 160 may also be stacked together in an alternating manner such that expansion of one compensates for contraction of its paired element.

In an ultrasonic instrument such as the instruments illustrated in FIG. 1 and in FIG. 2, power is transmitted to the surgical tip by setting up an acoustic standing wave in the stack. In order to generate a standing wave within a stack, the stack is designed to be a multiple of $\lambda_o/2$ in length where $\lambda_o$ is the wavelength of the fundamental frequency $f_o$. When the stack is designed to be $\lambda_o/2$ in length, a standing wave may be induced at the fundamental or any harmonic frequency. A minimum or zero crossing in the standing wave is generally referred to as a node. The physical positions along the length of the stack, transmission rod and surgical tip where the magnitude of the standing wave is a minimum may be referred to as node points. An absolute value maximum or peak in the standing wave is generally referred to as an anti-node. Therefore, the physical positions along the length of the stack, transmission rod and surgical tip where the magnitude of the standing wave is an absolute value maximum, may be referred to as anti-node points. Each end of the stack, being free to vibrate, is an anti-node point. Anti-nodes occur at intervals ½ wavelength along the length of the stack. In order to efficiently excite the stack and generate a standing wave at a desired excitation frequency, the excitation means, for example, the piezoelectric elements, are generally located at one or more node points. In any standing wave, a node is always located $\lambda/4$ from an anti-node. Therefore, since it is desirable to locate the piezoelectric section at an amplitude node, in a stack operating at a preselected frequency $f_x$ with associated wavelength $\lambda_x$, which is a harmonic of the fundamental frequency $f_o$ of the stack, the piezoelectric region may be located at a distance of approximately $\lambda_x/4$ from either end of the stack.

Where the stack is excited at the fundamental frequency, or at any odd whole integer multiple of the fundamental frequency, the standing wave generated in the stack will have a node at a distance of $\lambda_o/4$ from either end of the stack and at intervals of $\lambda_o/2$ beyond that point. Therefore, if the desired excitation frequency is the fundamental frequency or an odd multiple of the fundamental, the piezoelectric region may be positioned at a distance of $A\lambda_o/4$ from either end of the stack where A is any odd whole integer. Positioning the piezoelectric section a distance of $A\lambda_o/4$, where A is an odd whole integer from either end of the stack has the advantage of allowing the operator to selectively drive the piezoelectric region at the fundamental frequency of the instrument or at any odd multiple of the fundamental frequency. Alternatively, the stack may be designed to operate at a specific frequency or at a harmonic frequency other than an odd whole multiple of the fundamental frequency. In that case, the piezoelectric section may be located at any node of the standing wave generated by the excitation signal. Since nodes are always located at a distance of $A\lambda_e/4$ where A is any odd whole integer and $\lambda_e$ is the excitation frequency, the piezoelectric section may be located at $A\lambda_e/4$ from either end of the stack. Therefore, if the excitation frequency $f_e$ is X times the fundamental frequency, nodes of the standing wave will be located at $\lambda_o/4x$.

In a stack with a length of $\lambda/2$, a standing wave with a wavelength of $\lambda$ will have an amplitude node at a distance of approximately $\lambda/4$ from the end of the stack. Since it is generally advantageous to locate the piezoelectric section at a point where their amplitude of the standing wave is at a minimum, the piezoelectric section in a stack having a length of $\lambda/2$ would normally be located in the center of the stack, a distance of approximately $\lambda/4$ from either end of the stack. In a stack which is longer than $\lambda/2$, the stack may be a whole odd integer multiple of $\lambda/2$ (i.e. $\lambda$, $3\lambda/2$, $5\lambda/2$, $7\lambda/2$ ... $A\lambda/2$)

In FIG. 1, $\lambda_o$ represents the wave length of the fundamental frequency $f_o$. As FIG. 1 illustrates, the center of the piezoelectric section 50 is approximately one quarter wave length ($\lambda_o/4$) from the first end 12 of conical resonator 20. Further, step junction 25 is approximately one quarter wave length ($\lambda_o/4$) from the center of piezoelectric section 50. In a conventional stack, the resonators have a uniform diameter which is substantially equal to the diameter of the piezoelectric elements. The physical length of the resonators in a stack will be a function of a number of variables, including the thickness of the piezoelectric section, the mass of the material used in the resonators and the fundamental frequency of the stack. However, the length of the resonators is selected such that the stack in FIG. 1 is approximately one-half wave length ($\lambda/2$) long.

Figure 6:
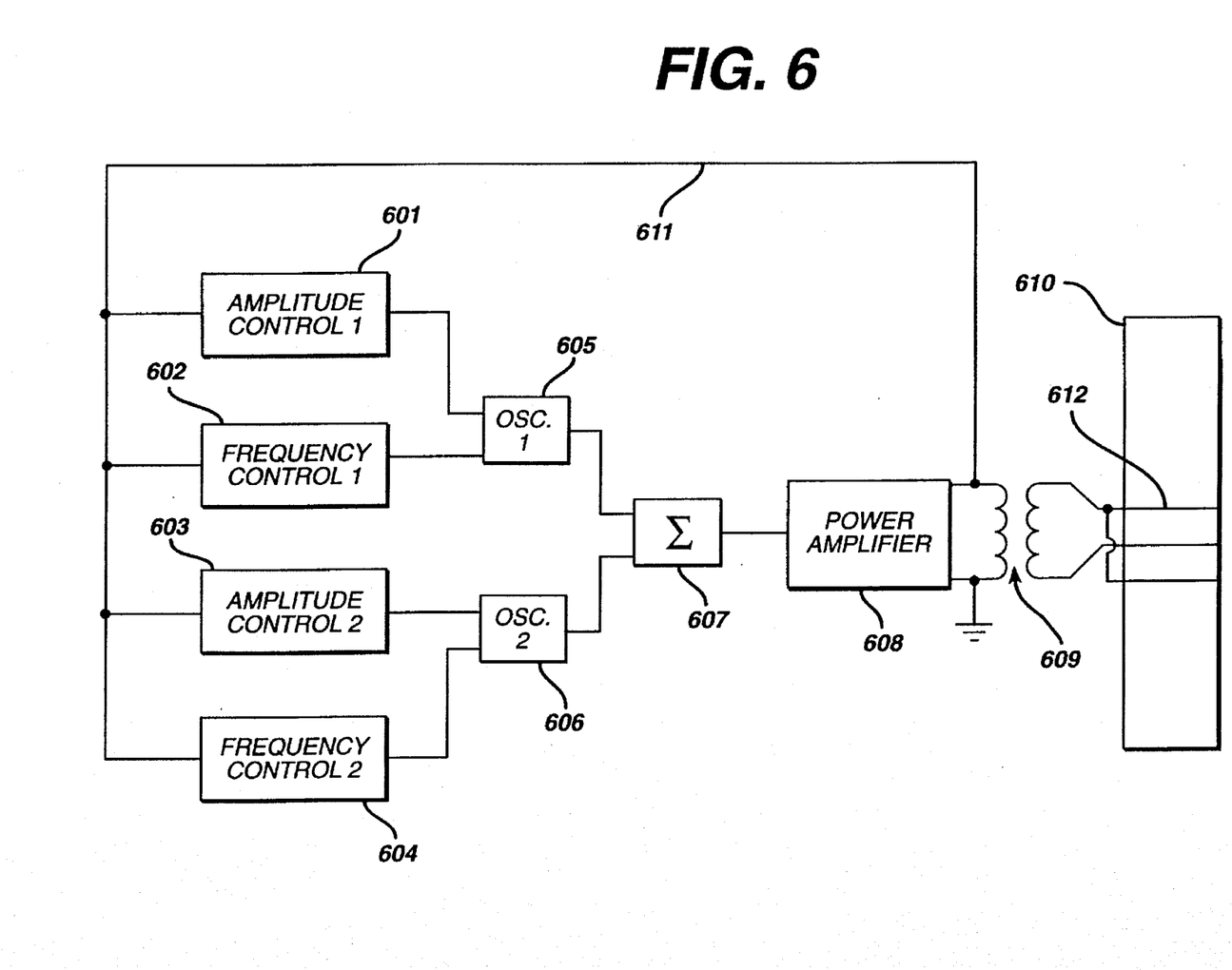
FIG. 6 illustrates a control system for use in conjunction with the surgical instrument illustrated in FIG. 1.

In the embodiment illustrated in FIG. 1, the electrical signal provided by signal wire 16 comprises at least a first and second excitation signals. The frequency $f_1$ of the first excitation signal is an odd whole integer multiple of the fundamental frequency $f_o$ (e.g. $f_o$, $3f_o$, $5f_o$, $7f_o$ ... ). The frequency $f_2$ of the second excitation signal is also an odd whole integer multiple of the fundamental frequency $f_o$, where $f_2$ is not equal to $f_1$. Thus, piezoelectric region 50 is being excited at $f_1$ and $f_2$ and is generating standing acoustic waves in stack 10 at $f_1$ and $f_2$. As a result, acoustic power transmitted by surgical tip 40 to the surrounding tissue has a component at $f_1$ and a second component at $f_2$. In the embodiment of FIG. 1, the power supply illustrated in FIG. 6 is designated to generate electrical excitation signals at both $f_1$ and $f_2$ such that the acoustic power delivered at $f_1$ is substantially equal to or greater than the power delivered at $f_2$. Alternatively, the power delivered at $f_1$ within 75% of the power delivered at $f_2$. Alternatively, the power delivered at $f_1$ may be adjusted with respect to the power delivered at $f_2$. The elements described and illustrated In FIG. 1 may be appropriately sized for particular applications by multiplying the dimension set forth above by any whole integer.

In FIG. 2, stack 110 is approximately $\lambda_o$ in length where $\lambda_o$ represents the wave length of the fundamental frequency $f_o$. In FIG. 2, piezoelectric sections 150 and 162 are located at node points. As FIG. 2 illustrates, the center of the piezoelectric section 150 is approximately one quarter wave length ($\lambda_o/4$) from the end 112 of resonator 120. Further, step junction 125 is approximately one quarter wave length ($\lambda_o/4$) from the center of piezoelectric section 162. Piezoelectric sections 150 and 160 are approximately one half ($\lambda/2$) wave length apart. The physical length of resonators 150 and 162 and central section 145 in a stack will be a function of a number of variables, including the thickness of the piezoelectric section, the mass of the material used in the resonators and the fundamental frequency of the stack at the tip. However, length of the central section and the resonators is selected such that the stack in FIG. 2 is approximately one wave length ($\lambda_o$) long.

Figure 7:
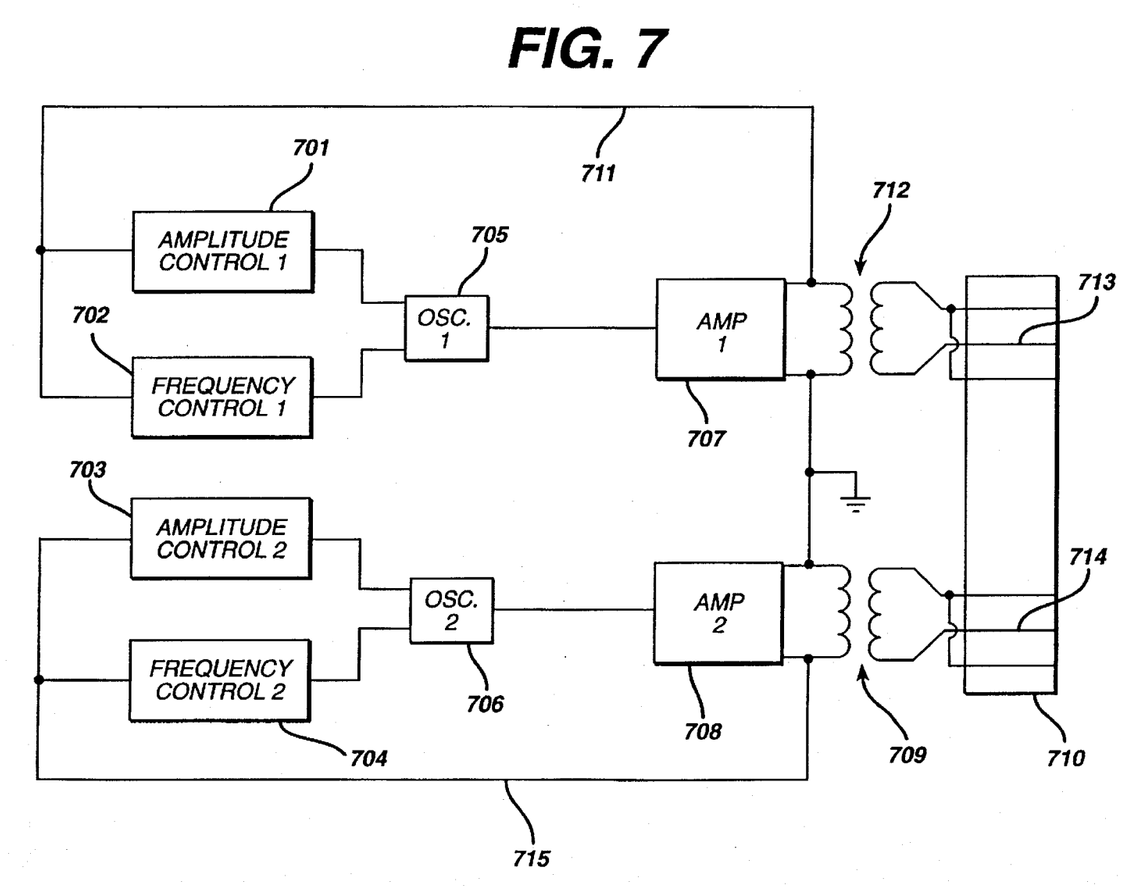
FIG. 7 illustrates a control system to use in conjunction with the surgical instruments illustrated in FIG. 2 and FIG. 3.

In the embodiment illustrated in FIG. 2, the electrical signal provided by signal wire 116 comprises at least first and second electrical excitation signals. The frequency $f_1$ of the first excitation signal is an odd whole integer multiple of the fundamental frequency $f_o$ (e.g. $f_o$, $3f_o$, $5f_o$, $7f_o$ . . .). The frequency of the second excitation signal is also an odd whole integer multiple of the fundamental frequency $f_o$ where $f_1$ is not equal to $f_2$. In the embodiment illustrated in FIG. 2, excitation signal $f_1$ excites the piezoelectric elements in first piezoelectric section 110 and while excitation signal $f_2$ excites the piezoelectric elements in second piezoelectric section 162. In the embodiment illustrated in FIG. 2, the power supply illustrated in FIG. 7 is designed to generate electrical excitation signals at both $f_1$ and $f_2$ such that the acoustic power delivered at $f_1$ is substantially equal to the power delivered at $f_2$. Alternatively, the power delivered at $f_1$ is within 75% of the power delivered at $f_2$. Alternatively, the power delivered at $f_1$ may be adjusted with respect to the power delivered at $f_2$.

In the embodiment illustrated in FIG. 2, first 150 and second 162 piezoelectric sections are located approximately $\lambda_o/4$ from first end 112 and step junction 125 respectively. Alternatively, as described herein, piezoelectric sections 150 and 162 may be located at any node point of the fundamental frequency. By selecting a node point of the fundamental frequency, a standing wave will be established when the piezoelectric section is excited at any odd whole integer multiple of the fundamental frequency. Thus, a single stack may be used to drive the surgical tip at one or more of such odd whole integer multiples of the fundamental frequency. If, however, the surgical tip is to be driven at a harmonic which is not an odd whole integer multiple of the fundamental, the location of the piezoelectric region must be selected according to the position of the nodes of the standing wave of the selected frequency as described herein. Therefore, in one embodiment of a stack wherein the position of the piezoelectric section is selected to coincide with a node point at the excitation frequency, the piezoelectric section may be positioned at a distance of $A\lambda_e/4$ from either end of the stack, where A is any odd whole integer and $\lambda_e$ is the wavelength of the excitation frequency $f_e$. Where multiple excitation signals are applied to separate piezoelectric sections, each individual piezoelectric section may be located at a distance of $A\lambda_e/4$ from either and of the stack, where A is an odd whole integer and $\lambda_e$ is the wavelength of the excitation frequency $f_e$ from that particular piezoelectric section. The elements described above and illustrated in FIG. 2 may be appropriately sized for particular applications by multiplying the dimensions set forth above by any whole integer.

Figure 3:
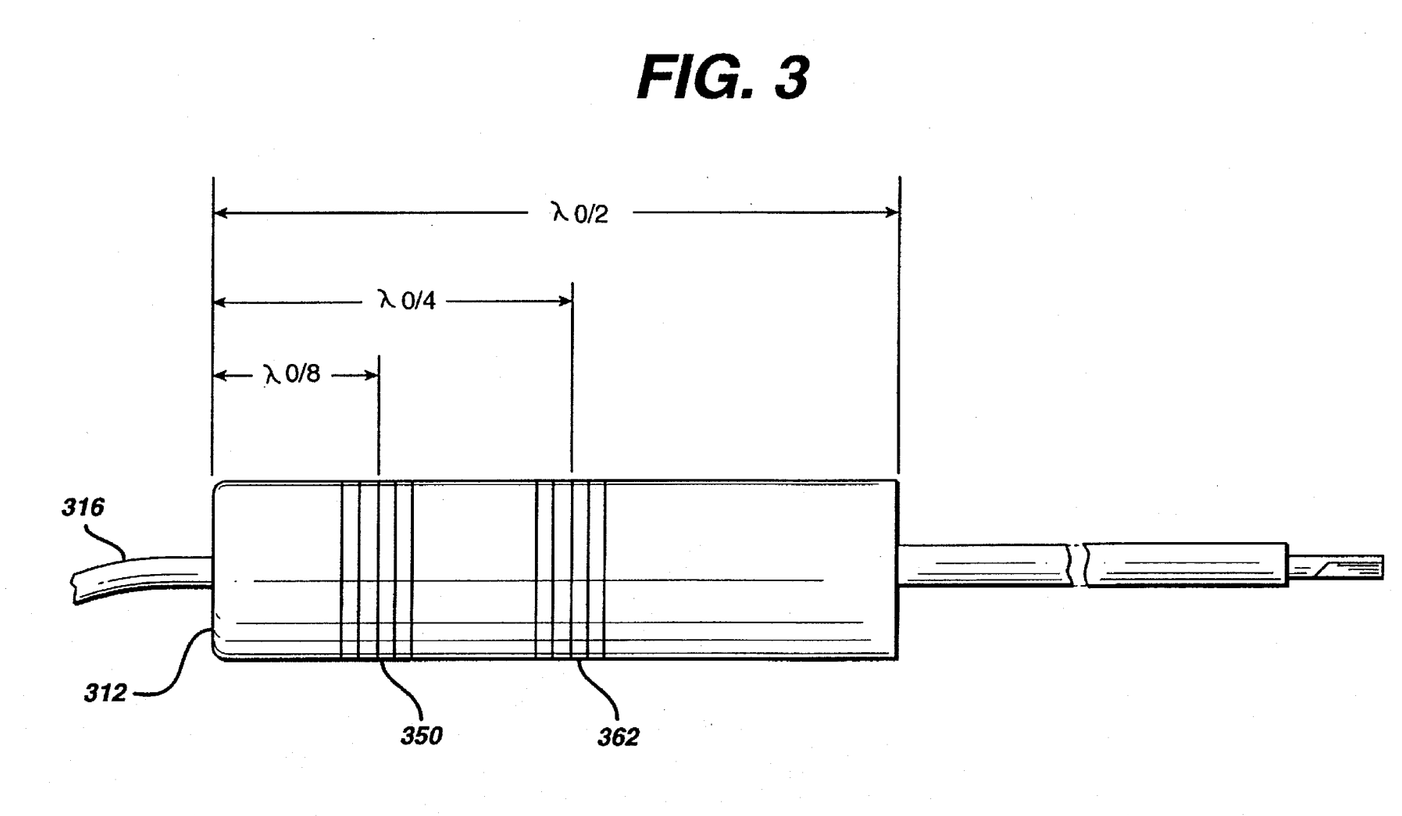
FIG. 3 is a side view of a further embodiment of a surgical instrument including two piezoelectric sections.

FIG. 3 is a side view of a further embodiment of the present invention wherein the piezoelectric sections are located at a distance of approximately $\lambda_o/8$ and $\lambda_o/4$ from the proximal end of the stack. The instrument illustrated in FIG. 3 is substantially identical to the instrument illustrated in FIG. 2 and the discussion of the elements in FIG. 2 applies to like elements in FIG. 3. In the embodiment illustrated in FIG. 3, the electrical signal provided by signal wire 316 comprises at least first and second electrical excitation signals. The frequency $f_1$ of the first excitation signal is an even whole integer multiple of the fundamental frequency $f_o$ (e.g. $f_o$, $2f_o$, $4f_o$, $6f_o$ . . .). The frequency of the second excitation signal is an odd whole integer multiple of the fundamental frequency $f_o$ where $f_1$ is not equal to $f_2$. In the embodiment illustrated in FIG. 3, excitation signal $f_1$ excites the piezoelectric elements in first piezoelectric section 350 and while excitation signal $f_2$ excites the piezoelectric elements in second piezoelectric section 362. In the embodiment illustrated in FIG. 3, the power supply illustrated in FIG. 7 is designed to generate electrical excitation signals at both $f_1$ and $f_2$ such that the acoustic power delivered at $f_1$ is substantially equal to the power delivered at $f_2$. Alternatively, the power delivered at $f_1$ is within 75% of the power delivered at $f_2$. Alternatively, the power delivered at $f_1$ may be adjusted with respect to the power delivered at $f_2$.

In the embodiment illustrated in FIG. 3, first piezoelectric section 150 is located approximately $\lambda_o/8$ from first end 112 while second piezoelectric section 162 is located a distance of approximately $\lambda_o/4$ from first end 112. If, however, the surgical tip is to be driven at a harmonic which is not an odd whole integer multiple of the fundamental, the location of the piezoelectric region must be selected according to the position of the nodes of the standing wave of the selected frequency as described herein. Therefore, in one embodiment of a stack wherein the position of the piezoelectric section is selected to coincide with a node point at the excitation frequency, the piezoelectric section may be positioned at a distance of $A\lambda_e/8$ from either end of the stack, where A is any odd whole integer and $\lambda_e$ is the wavelength of the excitation frequency $f_e$ for that piezoelectric section. Where multiple excitation signals are applied to separate piezoelectric sections, the second piezoelectric section may be located at a distance of $A\lambda_e/4$ from either and of the stack, where A is an odd whole integer and $\lambda_e$ is the wavelength of the excitation frequency $f_e$ for that particular piezoelectric section. The elements described above and illustrated in FIG. 3 may be appropriately sized for particular applications by multiplying the dimensions set forth above by any whole integer.

Figure 4A:
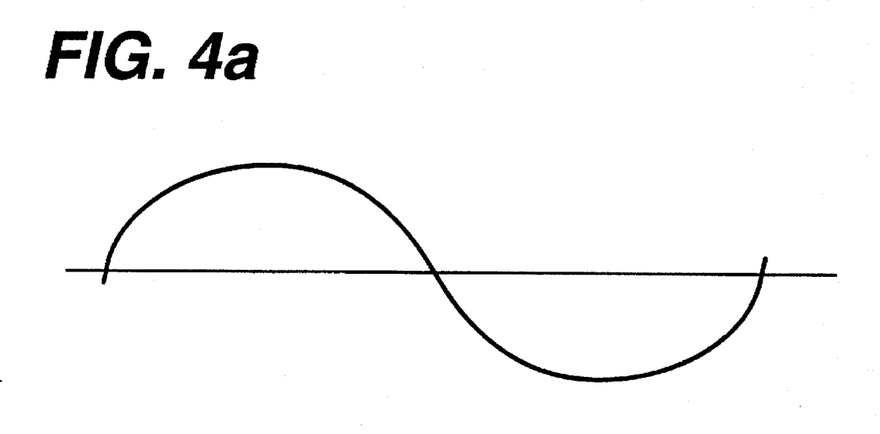
FIG. 4 illustrates a series of excitation waveforms including a fundamental frequency, a first harmonic and a signal composed of the algebraic sum of the fundamental and the first harmonic.
Figure 4B:
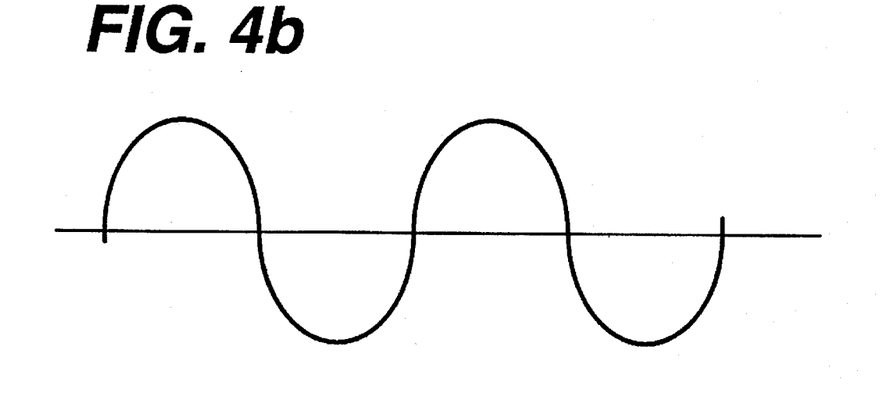
Figure 4C:
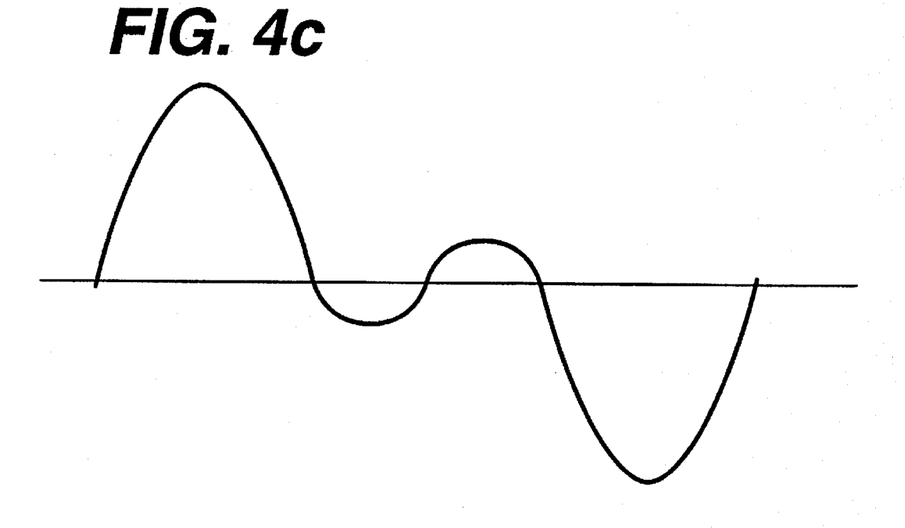

FIG. 4 illustrates a series of excitation waveforms. FIG. 4(a) illustrates a first sinusoidal excitation waveform which may have a frequency of, for example, 25 kHz. FIG. 4(b) illustrates a second sinusoidal excitation waveform which may have a frequency of, for example 50 kHz. The sinusoidal signals illustrated in FIGS. 4(a) and 4(b) are approximately equal in magnitude. FIG. 4(c) illustrates a waveform which represents the algebraic sum of the excitation signals in FIGS. 4(a) and 4(b). Thus, by driving the piezoelectric elements in a region 50 of FIG. 1 at the fundamental frequency, for example, the sinusoidal excitation waveform illustrated on FIG. 4(a), and a second or higher harmonic of the fundamental frequency, for example, the sinusoidal excitation waveform illustrated in FIG. 4(b), the surgical tip 40 is excited at both frequencies.

Figure 5:
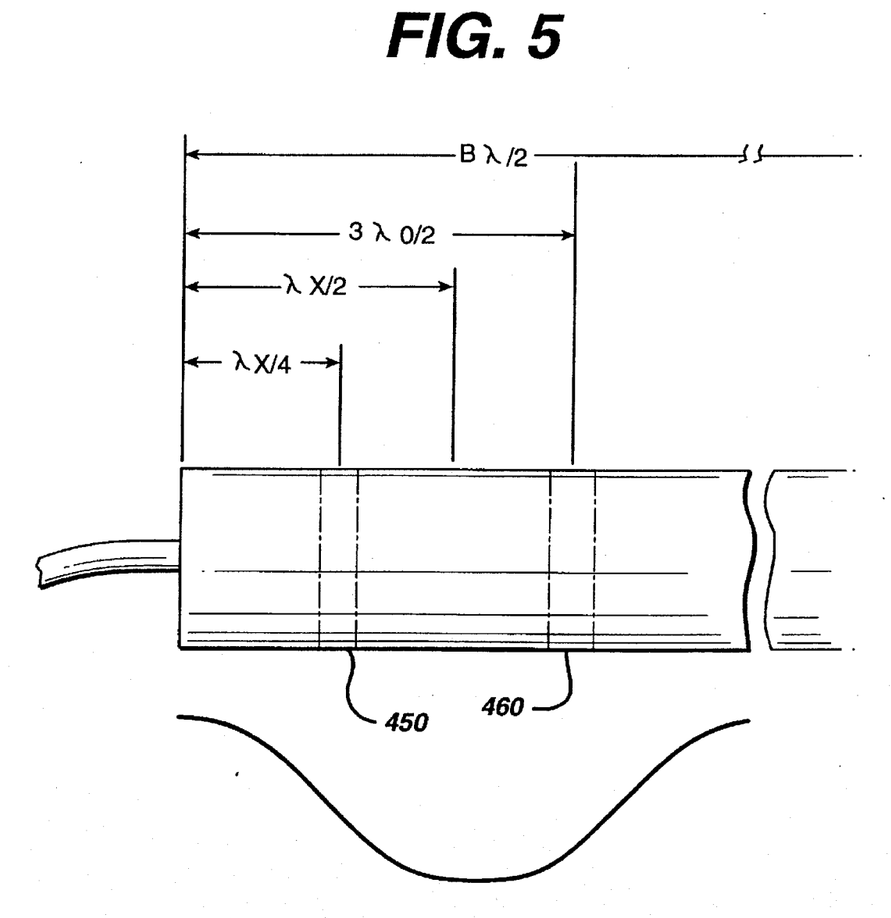
FIG. 5 is a schematic illustration of an embodiment of the present invention illustrating the potential location of piezoelectric sections.

FIG. 5 illustrates how the location of a piezoelectric section may be selected for a particular frequency $\lambda_x$. In FIG. 5 piezoelectric regions may be located at $\lambda_x/4$, $3\lambda_x/4$ etc, which correspond to node points for the standing wave generated at $f_x$.

FIG. 6 illustrates a control system for use with the instrument illustrated on FIG. 1. In FIG. 6, stack 610 includes a set of active elements (612) electrically coupled to impedance matching circuit 609. Power amplifier 608 receives a signal from summer 607, and outputs an amplified drive signal to matching circuit 609. Summer 607 adds signals $f_1$ from first oscillator 605 and $f_2$ from second oscillator 606. Feedback loop 611 provides input to first amplitude control circuit 601 and second amplitude control circuit 603 and, in addition, to first frequency control circuit 602 and second frequency control circuit 604 which drive first oscillator 605 and second oscillator 606 respectively.

FIG. 7 illustrates a control circuit for use with the instrument illustrated in FIGS. 2 and 3. In FIG. 6, stack 710 includes 2 sets of active elements 713 and 714 electrically coupled to separate impedance matching circuits 709 and 712. Power amplifiers 707 and 708 receive signals from oscillators 705 and 706 respectively, and output amplified drive signals to matching circuits 712 and 709 respectively. Oscillator 705 provides signal $f_1$ to amplifier 707. Oscillator 706 provides signal $f_2$ to amplifier 708. Feedback loop 711 provides input to amplitude control circuit 701 and frequency control (702) which drive oscillator 705. Feedback loop 715 provides input to amplitude control circuit 703 and frequency control circuit 704 which drives oscillator 706.

It will be recognized by those skilled in the art that many excitation sources, for example generators, do no produce clean sinusoidal waveforms such as the waveform illustrated in FIG. 3. Where the driving signal is not a clean sinusoidal waveform, the excitation signal will include both the fundamental frequency and one or more harmonic frequencies. In such signals, the harmonic elements are substantially lower in magnitude than the fundamental (e.g. usually less than 25% of the power of the fundamental), making any tip displacement at a harmonic relatively small compared with the tip displacement resulting from the fundamental excitation. By deliberately driving the harmonics of the excitation signal at a signal level which is 50% or more of and preferably equal to the signal level of the fundamental frequency, the magnitude of the tip displacement is substantially increased at the harmonic frequencies, substantially improving certain qualities of the instrument. For example, where the instrument is used as a knife when driver at the fundamental frequency, hemostatic properties of the instrument may be improved by increasing the magnitude of the excitation signal at the first or second harmonic of the fundamental frequency. In an alternate embodiment of the present invention, the phase of the harmonic excitation signal is continuously shifted with respect to the phase of the fundamental frequency. The resulting displacement of the surgical tip may enhance the instruments properties as a morcillator.

While the stack, according to the present invention, has been illustrated and described in conjunction with a transmission rod and a surgical cutting or dissecting tip, it will be apparent to those of skill in the art that a handpiece according to the present invention may be used in any number of ultrasonic surgical instruments. A stack, according to the present invention, might, for example, be used as a handpiece for ultrasonic surgical scissors or as a portion of the obturator in an ultrasonic trocar. In addition, a stack according to the present invention might be used as a hand piece for an ultrasonic cauterizing tool. Thus, the surgical tip described herein may represent a number of ultrasonic surgical tools, including those described herein.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. A method of exciting an ultrasonic stack in a surgical instrument wherein said stack includes a piezoelectric section located between a first and a second resonator wherein said method comprises the steps of:

exciting said piezoelectric section by driving said section with an electrical excitation signal at a first frequency; and simultaneously exciting said piezoelectric section by driving said section with an electrical excitation signal at a second frequency which is a multiple of said first frequency.

2. A method of exciting a stack according to claim 1 wherein said second frequency is approximately twice said first frequency.

3. A method of exciting a stack according to claim 2 wherein said stack has a fundamental frequency and said first frequency is said fundamental frequency.

4. A method of exciting a stack according to claim 1 wherein the input power of said signal at said second frequency is greater than or equal to 50% of the input power of said signal at said first frequency.

5. A method of exciting a stack according to claim 1 wherein said input power of said signal at said first frequency is greater than or equal to 50% of the input power of said signal at said second frequency.

6. An ultrasonic surgical instrument comprising:

a piezoelectric section between a first and a second resonator;

an power source attached to said piezoelectric section wherein said power source simultaneously supplies said piezoelectric section with an excitation signal comprising at least a first signal at a first frequency and a second signal at a second frequency wherein said second frequency is an integer multiple of said first frequency.

7. An ultrasonic instrument according to claim 6 wherein said second frequency is approximately twice said first frequency.

8. An ultrasonic stack according to claim 7 wherein said stack has a fundamental frequency and said first frequency is said fundamental frequency.

9. Ultrasonic instrument according to claim 6 wherein the input power of said signal at said second frequency is greater than or equal to 50% of the input power of said signal at said first frequency.

10. An ultrasonic stack according to claim 6 wherein said input power of said signal at said first frequency is greater than or equal to the input power of said signal at said second frequency.

11. An ultrasonic stack comprising:

a first piezoelectric section;

a second piezoelectric section;

a first resonator abutting a first side of said first piezoelectric section;

a second resonator abutting a second side of said first piezoelectric section and a first side of said second piezoelectric section; and a third resonator abutting a second side of said second piezoelectric section.

12. An ultrasonic stack according to claim 11 wherein said first piezoelectric section receives a drive signal at a first frequency and a said second piezoelectric section receives a drive signal at a second frequency different from said first frequency.

13. An ultrasonic stack according to claim 12 wherein said second frequency is a whole number multiple of said first frequency.

14. An ultrasonic stack according to claim 13 wherein said first piezoelectric section is located at a distance of approximately $A\lambda/4$ from one end of said stack where A is an odd integer and $\lambda_1$ is the wavelength of said first frequency.

15. An ultrasonic stack according to claim 14 which said second piezoelectric section is located at a distance of approximately $B\lambda/4$ from one end of said stack where B is an odd integer and $\lambda_1$ is the wavelength of said second frequency.

16. An ultrasonic stack according to claim 11 wherein said first piezoelectric section is located a distance of approximately $C\lambda/8$ from one end of the stack where C is an even integer.

17. An ultrasonic stack according to claim 11 wherein said first piezoelectric section is located a distance of approximately $C\lambda/8$ from one end of said stack and said second piezoelectric section is located a distance of approximately $D\lambda/8$ from said one end of said stack where C and D are any even integer and C is not equal to D.

* * * * *